US008044662B2

(12) United States Patent
Fransson et al.

(10) Patent No.: US 8,044,662 B2
(45) Date of Patent: Oct. 25, 2011

(54) ESTIMATING T2-DIFFUSION PROBABILITY DENSITY FUNCTIONS FROM NUCLEAR MAGNETIC RESONANCE DIFFUSION MODULATED AMPLITUDE MEASUREMENTS

(75) Inventors: Carl-Magnus Fransson, Cleveland, TX (US); Carla B. Hara Fransson, legal representative, Cleveland, TX (US); Ronald E. Cherry, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 26 days.

(21) Appl. No.: 12/541,323

(22) Filed: Aug. 14, 2009
(Under 37 CFR 1.47)

(65) Prior Publication Data
US 2010/0259258 A1     Oct. 14, 2010

Related U.S. Application Data

(63) Continuation of application No. 12/327,390, filed on Dec. 3, 2008, now abandoned, which is a continuation of application No. 11/997,995, filed as application No. PCT/US2006/021973 on Jun. 6, 2006, now abandoned.

(51) Int. Cl.
*G01V 3/00*     (2006.01)
(52) U.S. Cl. ............................ 324/303; 324/307; 702/12
(58) Field of Classification Search .................. 324/303
See application file for complete search history.

(56) References Cited

U.S. PATENT DOCUMENTS

| | | | | |
|---|---|---|---|---|
| 5,792,072 A | * | 8/1998 | Keefe ............................ | 600/559 |
| 6,226,418 B1 | * | 5/2001 | Miller et al. ................... | 382/294 |
| 6,271,522 B1 | * | 8/2001 | Lindermeir et al. ....... | 250/341.1 |
| 6,466,013 B1 | * | 10/2002 | Hawkes et al. ................ | 324/303 |
| 6,633,686 B1 | * | 10/2003 | Bakircioglu et al. .......... | 382/294 |
| 6,960,913 B2 | | 11/2005 | Heaton | |
| 2003/0071617 A1 | * | 4/2003 | Kruspe et al. .................. | 324/303 |
| 2004/0182606 A1 | * | 9/2004 | Goldman et al. ............... | 175/39 |
| 2004/0196038 A1 | * | 10/2004 | Kruspe et al. .................. | 324/303 |
| 2005/0040822 A1 | * | 2/2005 | Heaton .......... | 324/307 |
| 2005/0104587 A1 | * | 5/2005 | Akkurt .......... | 324/303 |
| 2007/0083114 A1 | * | 4/2007 | Yang et al. ..................... | 600/437 |
| 2009/0248311 A1 | * | 10/2009 | Coope et al. .................... | 702/13 |

FOREIGN PATENT DOCUMENTS
WO    WO-2007142636 A1    12/2007

OTHER PUBLICATIONS

"International Application No. PCT/US06/21973, International Search Report mailed Jun. 22, 2007", 2 pgs.
"International Application No. PCT/US06/21973, Written Opinion mailed Jun. 22, 2007", 8 pgs.

* cited by examiner

*Primary Examiner* — Melissa Koval
*Assistant Examiner* — Benjamin M Baldridge
(74) *Attorney, Agent, or Firm* — Schwegman, Lundberg & Woessner, P.A.

(57) ABSTRACT

In some embodiments, apparatus and systems, as well as methods, may operate to acquire data representing a plurality of nuclear magnetic resonance (NMR) echo trains associated with a material, such as a geological formation. Additional operations may include inverting a model of at least one of the plurality of NMR echo trains to provide an estimated distribution of transverse relaxation time constants, inverting models of selected ones of the plurality of NMR echo trains using the estimated distribution of transverse relaxation time constants to provide an estimated diffusion distribution, and inverting a model of selected ones of the plurality of NMR echo trains, using the estimated distributions of transverse relaxation time constants and diffusion, to provide an apparent and an intrinsic probability density function to identify fluid types in the material.

25 Claims, 9 Drawing Sheets

ESTIMATING T2-DIFFUSION PROBABILITY DENSITY FUNCTIONS FROM NUCLEAR MAGNETIC RESONANCE DIFFUSION MODULATED AMPLITUDE MEASUREMENTS

This application is a continuation of U.S. patent application Ser. No. 12/327,390, filed Dec. 3, 2008 now abandoned, which is a continuation of U.S. patent application Ser. No. 11/997,995, filed Feb. 5, 2008 now abandoned, which application is a U.S. National Stage Filing under 35 U.S.C. 371 from International Application Number PCT/US2006/021973, filed Jun. 6, 2006 and published in English as WO 2007/142636 A1 on Dec. 13, 2007, which applications and publication are incorporated herein by reference in their entirety.

TECHNICAL FIELD

Various embodiments described herein relate to the characterization of different types of matter, including apparatus, systems, and methods used to determine fluid types that may be present in various geological formations.

BACKGROUND INFORMATION

Fluid types (e.g., oil, water, gas) may exist in a variety of materials, including geological formations, and can be identified using nuclear magnetic resonance (NMR) diffusion modulated amplitude (DMA) data to compute a probability density function, which may be expressed as a graph illustrating porosity as a function of diffusion in $cm^2/sec$ and transverse relaxation time in milliseconds (e.g., using a what is known to those of skill in the art as a "$T_2$-D map"). Interested readers may refer to U.S. Pat. No. 6,512,371 (incorporated herein by reference in its entirety) describing how nuclear magnetic resonance DMA data are acquired.

Due to the huge amounts of data typically involved in calculating the function, reduction algorithms are commonly applied to reduce the computational intensity of the problem, which may take the general form: $M(t_D,t)=\iint \kappa_2(t,T_2) \cdot f(D, T_2) \cdot \kappa_1(t_D,D) dD dT_2$. Interested readers may refer to U.S. Pat. No. 6,462,542 (incorporated herein by reference in its entirety) describing how $T_2$-D maps may be calculated using a compression algorithm.

For example, incorporating the singular value decomposition of kernel matrices $K_1$ (the discrete diffusion kernel) and $K_2$ (the discrete relaxation kernel) into a compression algorithm, along with selecting a threshold condition number for the matrix $K_0 = K_1 \otimes K_2$, yields a projection of the data onto the range space while preserving the Frobenius norm of the data matrix. Unfortunately, once the original data is compressed, the original values are lost. In addition, this method is limited to using a zero-order regularization matrix for the probability density function, and independent regularization of the transverse relaxation time constant distribution and diffusion distribution is not possible.

DETAILED DESCRIPTION

In some embodiments of the invention, the challenges described above may be addressed by computing two dimensional apparent and intrinsic probability density functions (e.g., $T_2$-D maps) from standard NMR diffusion modulated amplitude measurements, using estimated distributions of transverse relaxation time constants and diffusion. The objective of making such measurements in a well, as might occur in a petrochemical recovery operation, is to locate zones in a geological formation that contain fluid for production, as well as to identifying the fluid type (e.g., oil vs. gas). For the purposes of this document, a "fluid" is any material that has an NMR transverse relaxation time constant of greater than 1 millisecond. The measurements can be used to establish the ultimate value of the well (e.g., potential volume of oil/gas to be recovered, and speed of recovery). In addition, when openhole logs are made, decisions are made as to whether to plug the well, or to complete it. The type of completion is different for different fluids, such that completing a gas well is different than completing an oil well, and oil wells differ with respect to light oil and heavy oil. Thus, accurate fluid typing can facilitate these decisions.

The following variables are defined for the purposes of this document:

$a_d$=direct echo calibration constant, a response that results directly from the initial pulse (i.e., the direct echo) [unitless]
$a_s$=stimulated echo calibration constant, a response that may result from a combination of pulses after the direct echo (i.e., the indirect echo) [unitless]
D=diffusion coefficient [$cm^2/s$]
f=continuous two-dimensional probability density function [unitless]
G=magnetic field gradient [G/cm]
$K_1$=discrete diffusion kernel [unitless]
$K_2$=discrete relaxation kernel [unitless]
$K_{2d}$=discrete diffusion kernel [unitless]
$L_x$=regularization matrix [unitless]
M=response from a diffusion modulated amplitude (DMA) sequence [unitless]
m=number of inverted echoes in an echo train from a diffusion modulated amplitude (DMA) sequence [unitless]
$n_1$=number of discretized values in a diffusion distribution [unitless]
$n_2$=number of discretized values in a relaxation distribution [unitless]
p=number of echo trains with different initial echo spacing [unitless]
t=measurement time [ms]
$t_E$=short echo spacing [ms]
$t_D$=long echo spacing [ms]
$t_{Dk}$=long echo spacing for echo train k [ms]
$T_2$=transverse relaxation time constant [ms]
X=discrete two-dimensional probability density function [unitless]
x=vectorized version of X [unitless]
$x_{T0}$=estimated $T_2$ distribution [unitless]
$x_T$=$T_2$ distribution [unitless]
$x_{D0}$=estimated diffusion distribution [unitless]
$x_D$=diffusion distribution [unitless]

Y=matrix of measured echoes [unitless]
y=vectorized version of Y [unitless]
$\alpha_x$=regularization parameter [unitless]
$\kappa_1$=continuous diffusion kernel [unitless]
$\kappa_2$=continuous relaxation kernel [unitless]
$\gamma=2\pi 4258$=gyromagnetic ratio [Hz/G]

In the standard DMA measurement process, p>2 NMR echo trains are typically acquired. Estimating a useful $T_2$-D map typically requires p>2 because p=2 permits only an average diffusivity value to be estimated, and p=3 permits obtaining only two points of the diffusivity distribution.

The first two echoes of echo train k have an echo spacing of $t_{Dk}$ and the remaining echoes have an echo spacing of $t_E$ (i.e., minimal echo spacing). Echo trains with relatively small values of $t_D$, (but larger than $t_E$), such as about $2*t_E$, are used to identify relatively diffusive fluids (e.g., gas), and echo trains with relatively large values of $t_D$, such as about $50*t_E$, are used to identify fluids that are not so diffusive (e.g., heavy oil).

For each echo train k and $t>2 \cdot t_{Dk}$, the response $M(t_D,t)$ is related to the two-dimensional probability density function $f(D,T_2)$ by a Fredholm integral of the first kind:

$$M(t_D,t)=\iint \kappa_2(t,T_2) \cdot f(D,T_2) \cdot \kappa_1(t_D,D) dD dT_2, \quad (1)$$

where $\kappa_2 = e^{-t/T_2}$ and $$\kappa_1 = e^{-\frac{1}{6}\gamma^2 G^2 D t_D^3}$$

for homogeneous magnetic fields, and $$\kappa_1 = a_d e^{-\frac{1}{6}\gamma^2 G^2 D t_D^3} + a_s e^{-\frac{1}{3}\gamma^2 G^2 D t_D^3}$$

for inhomogeneous magnetic fields.

This is the case because in standard $T_2$ logging we have the relationship $M(t)=\int \kappa_2(T_2) \cdot f(T_2) dT_2$, where $\kappa_2 \cdot f$ is an exponential function describing the $T_2$ decay in the response M acquired with an echo spacing of $t_E$ (e.g., $t_E$ may be viewed as a sampling time interval). If the first two echoes in the echo train are acquired with echo spacing $t_D > t_E$ and the subsequent echoes are acquired with echo spacing $t_E$, the diffusivity of the measured fluid particles will determine the amount of additional signal amplitude lost during the first two echoes. This is described by the function $\kappa_1$. The probability density function $f(D,T_2)$ then describes how much of the signal amplitude corresponds to a particular combination of $T_2$ and D. $a_d$ and $a_s$ are tool-specific calibration constants, which can be determined a priori by performing measurements in a known fluid (e.g., water in a calibration tank) so that the tool's response can be characterized.

To simplify the problem of processing large amounts of NMR data, while still providing an accurate $T_2$-D map, the unknown parameters D and $T_2$ can be partitioned into $n_1$ and $n_2$ values respectively (where the number of values depends on the resolution desired for each axis of the $T_2$-D map) so that the only unknowns in equation (1) are the components in the function $f(D, T_2)$. In matrix notation, the discretized version of (1) can then be written as:

$$Y=K_2 X^T K_1^T, \quad (2)$$

where $Y \in \mathfrak{R}^{m \times p}$, $K_2 \in \mathfrak{R}^{m \times n_2}$, $X \in \mathfrak{R}^{n_1 \times n_2}$, and $K_1 \in \mathfrak{R}^{p \times n_1}$. As is known to those of skill in the art, $\mathfrak{R}$ is the mathematical notation for a set of real-valued numbers (i.e., the numbers are not in complex form). Thus, for example, Y comprises a real-valued matrix with m rows and p columns, where m denotes the number of echoes in each echo train.

In an optimization framework, the problem to determine X can be posed as:

$$X^* = \underset{X \geq 0}{\arg\min} \|Y - K_2 X^T K_1^T\|_F^2. \quad (3)$$

F is the mathematical notation that corresponds to the "Frobenius-norm" of a matrix, where the matrix norm is a measure of its magnitude. For example, the Frobenius-norm of a matrix X can be obtained by performing the calculation: $\sqrt{\text{sum}(\text{diag}(X'X))}$. Another commonly used norm is the "2-norm".

By lexicographically ordering the matrices Y and X into vectors (e.g., vectorizing), equation (3) can be reduced to a one-dimensional problem of the following vectorized form:

$$x^* = \underset{x \geq 0}{\arg\min} \|K_0 x - y\|_2^2, \quad (4)$$

where $K_0 \in \mathfrak{R}^{mp \times n_1 n_2} = K_1 \otimes K_2$, $x \in \mathfrak{R}^{n_1 n_2 \times 1}$, and $y \in \mathfrak{R}^{mp \times 1}$. Thus, x is a matrix with $n_1 * n_2$ rows and 1 column (i.e., a vector).

The matrices $K_1$ and $K_2$ are rank-deficient, and therefore the problem presented in equation (4) is ill-conditioned. To provide a well-conditioned problem, an additional regularization term is added to equation (4) as follows:

$$x^* = \underset{x \geq 0}{\arg\min} \|K_0 x - y\|_2^2 + \alpha_x \|L_x x\|_2^2, \quad (5)$$

where $\alpha_x$ is a regularization parameter determining the smoothness of the solution and $L_x \in \mathfrak{R}^{mp \times n_1 n_2}$ is a regularization matrix. In addition to regularizing the solution vector x, equation (5) can be extended to include explicit regularization terms for the $T_2$-distribution and the D-distribution, simply by adding additional terms which include predetermined regularization parameters $\alpha_{x_T}$ and $\alpha_{x_D}$, and regularization matrices $L_{x_T}$ and $L_{x_D}$. The resulting equation is:

$$x^* = \underset{x \geq 0}{\arg\min} \|K_0 x - y\|_2^2 + \alpha_x \|L_x x\|_2^2 + \alpha_{x_T} \|L_{x_T} x\|_2^2 + \alpha_{x_D} \|L_{x_D} x\|_2^2. \quad (6)$$

The regularization parameters $\alpha_x$, $\alpha_{x_T}$, and $\alpha_{x_D}$ can be used to determine how much smoothing will be applied to x and may be selected based on the noise level of the echo trains, if desired. Thus, if the signal-to-noise ratio (SNR) of the acquired NMR echo train data is low (i.e., the data is noisy), the alpha values should be large in order to provide a solution having the desired smoothness. If the SNR is relatively high (i.e., low noise level in the data) then smaller alpha values can be chosen to more easily resolve small components. Other methods of selecting alpha regularization parameter for these types of inversion problems may include trying many different values of alpha and then selecting one of them based on the pareto-optimum criteria. The matrices $L_{x_T}$ and $L_{x_D}$ may be selected a priori as matrices that operate on the second derivative of x. This choice can also can provide smoother solutions.

Equation (6) can be solved in a standard least-squares fashion, but may be computationally intensive and require significant amounts of system memory. For example, solving equation (6) with m=500, p=6, $n_1$=40, and $n_2$=40 can require a minute or two of computing time per level on a standard laptop computer. Since log data often involves thousands of levels, an improved method is desired.

To more efficiently solve equation (6), the problem can be reduced, if desired, by eliminating part of the potential solution space via two actions: a $T_2$ inversion and a D inversion. This is explained in detail below.

First, a $T_2$ inversion may be accomplished by realizing that any, or all, of the p echo trains from the DMA sequence can be used to estimate the $T_2$ distribution $x_{T0} \in \Re^{n \times 1}$ (which corresponds to the projection of the probability density function on the $T_2$ axis of a $T_2$-D map). To simplify the discussion, the reader is invited to consider the case where only one echo train is used, e.g., an echo train where $t_D \approx t_E$.

Estimating the $T_2$ distribution from a single echo train is a standard linear least-squares problem, well known to those of skill in the art, and will not be discussed in detail. Readers that desire to know more about how $T_2$ distributions can be estimated from a single echo train (as a standard least-squares problem) may consult "NMR Pore Size Distributions and Permeability at the Well Site" by Prammer, SPE paper 28368, 69$^{th}$ Annual Technical Conference and Exhibition, New Orleans, La., 1994; "Practical Optimization," by Gill et al., Academic Press, London and New York (1981); and the "User's guide for LSSOL (version 1.0): A Fortran package for Constrained Linear Least-Squares and Convex Quadratic Programming," by Gill et al., Technical Report SOL 86-1, Systems Optimization Laboratory, Dept. of Operations Research, Stanford University, 1986.

Second, a D inversion may be accomplished by replacing X in equation (6) with $x_{D0} x_{T0}^T$, where $x_{D0} \in \Re^{n1 \times 1}$ denotes an estimate of the diffusion distribution (i.e., the projection of the probability density function on the D axis of the $T_2$-D map). This also represents a standard linear least squares problem, which is readily solved by those of skill in the art. That is, mathematically, the problem has a structure that is very similar to that of estimating the $T_2$ distribution from a single echo train. Thus in this case, X is replaced by $X' = x_{D0} x_{T0}^T$, and $x' = \text{vec}(X')$ so that equation (6) becomes:

$$x'^* = \underset{x' \geq 0}{\arg\min} \|K_0 x' - y\|_2^2 + \alpha_x \|L_x x'\|_2^2 + \alpha_{x_T} \|L_{x_T} x'\|_2^2 + \alpha_{x_D} \|L_{x_D} x'\|_2^2 \quad (7)$$

Although $x_{T0}$ and $x_{D0}$ are now known as a result of the $T_2$ inversion and the D inversion, there are still many solutions x to the original problem presented by equation (6). However, the desired solution may be readily obtained by noting that $X(i,j)=0$ if $x_{T0}(i)=0$ or $x_{D0}(j)=0$ because $x_{T0}$ is the projection of the probability density function on the $T_2$-axis and $x_{D0}$ is the projection of the probability density function on the D-axis. This means that columns of the $K_1$ and $K_2$ matrices may be removed, and hence the $K_0$ matrix becomes smaller, resulting in reduced computation time by eliminating part of the potential solution space, when inverting for the probability density function.

Thus, as part of the final activity of inverting a model of echo trains for a probability density function, the vectorization of X for which $X(i,j)>0$ may be denoted by $\tilde{x}$, and the matrix containing the columns of $K_0$ corresponding to $x_{T0}>0$ and $x_{D0}>0$ may be denoted by $\tilde{K}_0$. Using the results obtained from the $T_2$ inversion and the D inversion, equation (6) can be re-written in its reduced form as follows:

$$\tilde{x}^* = \underset{\tilde{x} \geq 0}{\arg\min} \|\tilde{K}_0 \tilde{x} - y\|_2^2 + \tilde{\alpha}_x \|\tilde{L}_x \tilde{x}\|_2^2 + \tilde{\alpha}_{x_T} \|\tilde{L}_{x_T} \tilde{x}\|_2^2 + \tilde{\alpha}_{x_D} \|\tilde{L}_{x_D} \tilde{x}\|_2^2. \quad (8)$$

Equation (8) is readily solved with a standard linear least-squares algorithm using bound constraints on $\tilde{x}$ only, or if desired, additional constraints on $\tilde{x}$ can be added to ensure that the projection of X on the $T_2$- and D-axes of the $T_2$-D map equals $x_{T0}$ and $x_{D0}$ obtained from the $T_2$- and D-inversions. Solution methods for equation (8) as a standard linear least-squares problem are well-known to those of skill in the art. Readers may consult the references noted above for further information.

Any constant structure can be assumed for the regularization matrices $L_x$, $L_{x_T}$, and $L_{x_D}$, including a second order derivative approximation. Other approximations, among the many available, include an identity matrix or a first order derivative approximation. An example of a second order derivative approximation in eight unknowns (an arbitrary example) is:

$$\begin{bmatrix} 1 & -2 & 1 & 0 & 0 & 0 & 0 & 0 \\ 0 & 1 & -2 & 1 & 0 & 0 & 0 & 0 \\ 0 & 0 & 1 & -2 & 1 & 0 & 0 & 0 \\ 0 & 0 & 0 & 1 & -2 & 1 & 0 & 0 \\ 0 & 0 & 0 & 0 & 1 & -2 & 1 & 0 \\ 0 & 0 & 0 & 0 & 0 & 1 & -2 & 1 \end{bmatrix}$$

The solution to equation (8) or (6) is the vectorized version of the transpose of the apparent probability density function $X_A$, which can be represented by a $T_{2A}$-D map, where the word "apparent" refers to the $T_2$ axis being dependent on acquisition and tool parameters such as the echo spacing $t_E$ and the magnetic field gradient G. To enhance fluid typing capabilities, it may also be desirable to compute a probability density function which is independent of such parameters; this is denoted the intrinsic probability density function $X_I$, which can be represented by a $T_{2I}$-D map. To achieve an intrinsic probability density function, one may recall the well-known relationship between the apparent and intrinsic transverse relaxation time constants ($T_{2A}$ and $T_{2I}$ respectively) and the diffusion coefficient D:

$$\frac{1}{T_{2A}} = \frac{1}{T_{2I}} + \frac{D(G \gamma t_E)^2}{12} \quad (9)$$

After solving equation (8) or (6), the apparent probability density function $X_A$ is known and equation (9) can then be used to create a model of intrinsic echo trains $Y_I$ as follows:

$$Y_I = (K_2./K_{2d}) / X_A^T K_1^T, \quad (10)$$

where $K_{2d}$ is the discretized version of a diffusion kernel $\kappa_{2d} = e^{-tD(G \gamma t_E)^2}$, and where the operator "./" denotes element-wise division of two matrices. The intrinsic probability density function can then be obtained by replacing y in equation (6) with $y_I$ (the vectorized version of $Y_I$):

$$x_I^* = \underset{x \geq 0}{\arg\min} \|K_0 x - y_I\|_2^2 + \alpha_x \|L_x x\|_2^2 + \alpha_{x_T} \|L_{x_T} x\|_2^2 + \alpha_{x_D} \|L_{x_D} x\|_2^2. \quad (11)$$

To more efficiently solve equation (11), the problem can be reduced by eliminating part of the potential solution space via the knowledge of the apparent probability density function $X_A$. This is explained in detail below.

$x_D$ denotes the projection of the apparent probability density function on the D-axis and thus, $x_D(i)=0$ implies that row i of both $X_A$ and $X_I$ has to contain all zeroes (i.e. $X_A(i,:)=X_I(i,:)=0$). This means that the size of the $K_1$ matrix, and hence also the $K_0$ matrix, may be reduced, perhaps resulting in reduced computation time, by eliminating part of the potential solution space, when inverting to provide the intrinsic probability density function.

Thus, as part of the final activity of inverting a model of an intrinsic probability density function, the vectorization of $X_1$ for which $X_1(i,j)>0$ may be denoted by $\tilde{x}_1$ and the matrix containing the columns of $K_0$ corresponding to $x_D>0$ may be denoted by $\tilde{K}_{01}$. Equation (11) can now be re-written in its reduced form as follows:

$$\tilde{x}_I^* = \underset{\tilde{x}_I \geq 0}{\operatorname{argmin}} \left\| \tilde{K}_{0I}\tilde{x}_I - y_I \right\|_2^2 + \tilde{\alpha}_x \left\| \tilde{L}_x \tilde{x}_I \right\|_2^2 + \tilde{\alpha}_{xT} \left\| \tilde{L}_{xT} \tilde{x}_I \right\|_2^2 + \tilde{\alpha}_{xD} \left\| \tilde{L}_{xD} \tilde{x}_I \right\|_2^2 \quad (12)$$

Equation (12) is readily solved in the same manner as equation (8).

Figure 1:
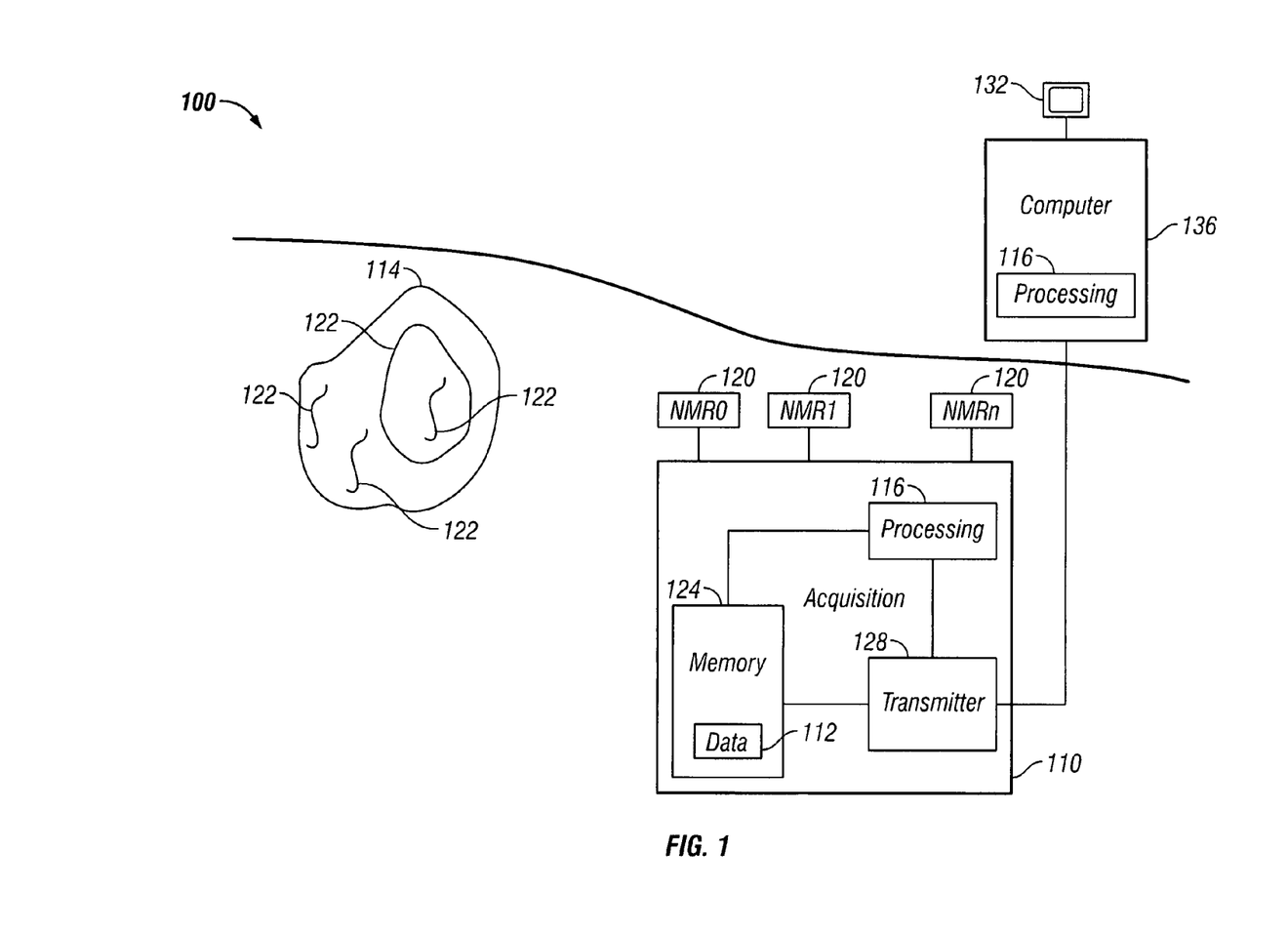
FIG. 1 illustrates an apparatus according to various embodiments of the invention.

To implement the solutions described, a variety of apparatus, systems, and methods may be used. For example, FIG. 1 illustrates an apparatus 100 according to various embodiments of the invention. In some embodiments, the fluid typing apparatus 100 may include acquisition logic 110 to acquire data 112 representing a plurality of nuclear magnetic resonance (NMR) echo trains associated with a material 114 (e.g., a geological formation, and/or liquids within a geological formation).

The apparatus 100 may also include processing logic 116 to invert a model of at least one of the plurality of NMR echo trains to provide an estimated distribution of transverse relaxation time constants (e.g., a $T_2$ inversion), to invert a model of selected ones of the plurality of NMR echo trains using the estimated distribution of transverse relaxation time constants to provide an estimated diffusion distribution (e.g., a D inversion), and to invert models of selected ones of the plurality of NMR echo trains, using the estimated distributions of transverse relaxation time constants and diffusion, to provide both an apparent and an intrinsic probability density function to identify fluid types 102 in the material 114.

In some embodiments, the apparatus 100 may comprise one or more NMR sensors 120 to receive signals 122 associated with the data 112. The apparatus 100 may comprise a memory 124 to store the data 112. The data 112, in turn, may include information associated with long echo spacing (e.g., $t_D$) and short echo spacing (e.g., $t_E$) for the plurality of NMR echo trains.

In some embodiments, the apparatus 100 may include a telemetry transmitter 128 to transmit the data 112, in compressed or uncompressed format, to a computer 136, such as an above-ground computer. The apparatus 100 may also include a display 132 to display visual representations of the apparent and intrinsic probability density functions, the apparent and/or intrinsic distributions of transverse relaxation time constants, and the diffusion distribution.

Figure 2A:
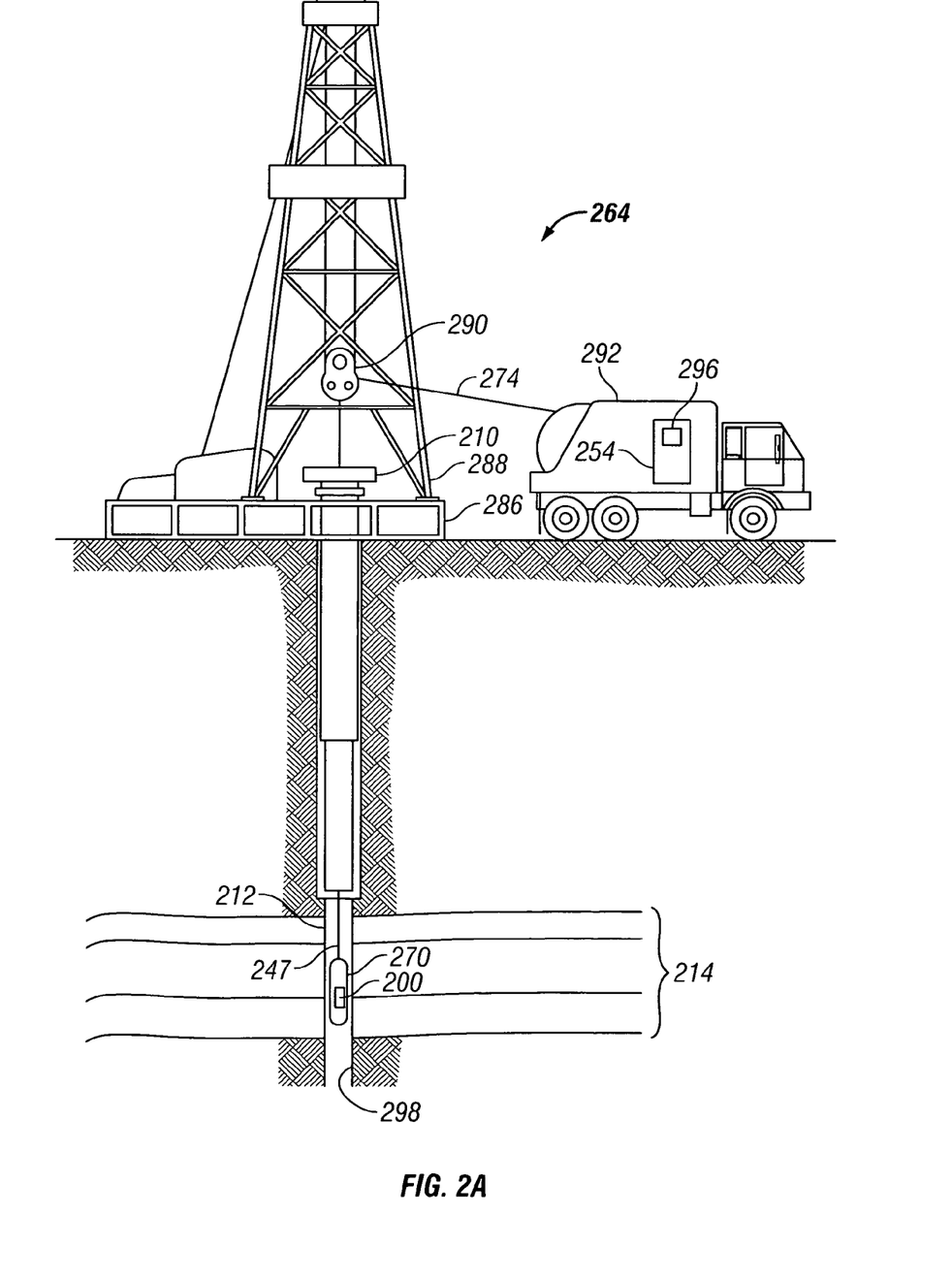
FIGS. 2A-2B illustrate apparatus and systems according to various embodiments of the invention.
Figure 2B:
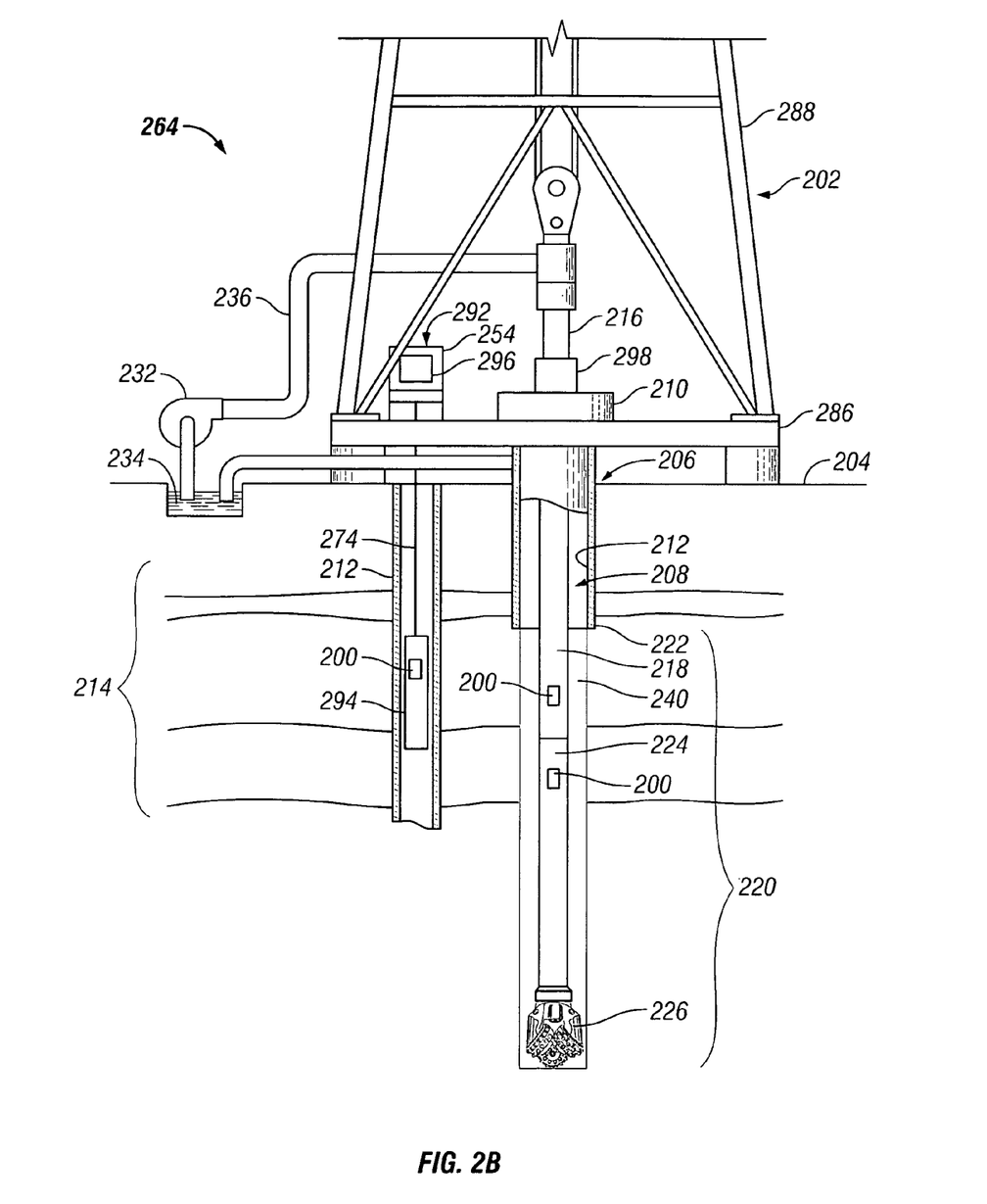

FIGS. 2A-2B illustrate apparatus 200 and systems 264 according to various embodiments of the invention. The apparatus 200, which may be similar to or identical to the apparatus 100 described above and shown in FIG. 1, may comprise portions of a tool body 270 as part of a wireline logging operation, or of a downhole tool 224 as part of a downhole drilling operation. For example, FIG. 2A shows a well during wireline logging operations. A drilling platform 286 may be equipped with a derrick 288 that supports a hoist 290. Drilling oil and gas wells is commonly carried out using a string of drill pipes connected together so as to form a drilling string that is lowered through a rotary table 210 into a wellbore or borehole 212.

Here it is assumed that the drilling string has been temporarily removed from the borehole 212 to allow a tool body 270 (e.g., a wireline logging tool), such as a probe or sonde, to be lowered by wireline or logging cable 274 into the borehole 212. Typically, the tool body 270 is lowered to the bottom of the region of interest and subsequently pulled upward at a substantially constant speed. During the upward trip, instruments included in the tool body 270 (e.g., apparatus 200) may be used to perform measurements on the subsurface formations 214 adjacent the borehole 212 as they pass by. The measurement data, including DMA NMR echo train data for a plurality of echo trains, can be communicated to a logging facility 292 for storage, processing, and analysis. The logging facility 292 may be provided with electronic equipment for various types of signal processing. Similar log data may be gathered and analyzed during drilling operations (e.g., during LWD operations). For example, the tool body 270 in this case may house one or more apparatus 200, and the logging facility 292 may include one or more surface computers 254, similar to or identical to the computer 136 described above with respect to FIG. 1.

Turning now to FIG. 2B, it can be seen how a system 264 may also form a portion of a drilling rig 202 located at a surface 204 of a well 206. The drilling rig 202 may provide support for a drill string 208. The drill string 208 may operate to penetrate a rotary table 210 for drilling a borehole 212 through subsurface formations 214. The drill string 208 may include a Kelly 216, drill pipe 218, and a bottom hole assembly 220, perhaps located at the lower portion of the drill pipe 218. The drill string 208 may include wired and unwired drill pipe, as well as wired and unwired coiled tubing.

The bottom hole assembly 220 may include drill collars 222, a downhole tool 224, and a drill bit 226. The drill bit 226 may operate to create a borehole 212 by penetrating the surface 204 and subsurface formations 214. The downhole tool 224 may comprise any of a number of different types of tools including MWD tools, LWD tools, and others.

During drilling operations, the drill string 208 (perhaps including the Kelly 216, the drill pipe 218, and the bottom hole assembly 220) may be rotated by the rotary table 210. In addition to, or alternatively, the bottom hole assembly 220 may also be rotated by a motor (e.g., a mud motor) that is located downhole. The drill collars 222 may be used to add weight to the drill bit 226. The drill collars 222 also may stiffen the bottom hole assembly 220 to allow the bottom hole assembly 220 to transfer the added weight to the drill bit 226, and in turn, assist the drill bit 226 in penetrating the surface 204 and subsurface formations 214.

During drilling operations, a mud pump 232 may pump drilling fluid (sometimes known by those of skill in the art as "drilling mud") from a mud pit 234 through a hose 236 into the drill pipe 218 and down to the drill bit 226. The drilling fluid can flow out from the drill bit 226 and be returned to the surface 204 through an annular area 240 between the drill pipe 218 and the sides of the borehole 212. The drilling fluid may then be returned to the mud pit 234, where such fluid is filtered. In some embodiments, the drilling fluid can be used to cool the drill bit 226, as well as to provide lubrication for the drill bit 226 during drilling operations. Additionally, the drilling fluid may be used to remove subsurface formation 214 cuttings created by operating the drill bit 226.

Thus, referring now to FIGS. 1 and 2A-2B, it may be seen that in some embodiments, the system 264 may include a drill collar 222, and a downhole tool 224, including a tool body 270 or a substantially permanently installed probe 294 (in a downhole well), to which one or more apparatus 200 are attached. The downhole tool 224 may comprise an LWD tool or MWD tool. The tool body 270 may comprise a wireline logging tool, including a probe or sonde, for example, coupled to a cable 274, such as a wireline or logging cable. Thus, a wireline 274 or a drill string 208 may be mechanically coupled to the downhole tool 224.

In some embodiments then, a system 264, such as a fluid typing system, may include a downhole tool 270 and acquisition logic 110 as described above and shown in FIG. 1. The acquisition logic 110, as well as any other part of the apparatus 100, 200, including the processing logic 116, may be housed by the downhole tool 270.

In some embodiments, the system 264 may include a drill bit 226 mechanically coupled to a drill string 208 and the downhole tool 224. The drill string may include one or more of segmented drilling pipe, casing, and/or coiled tubing. The system 264 may further include a steering mechanism 298 to steer the drill bit 226 responsive to the apparent and/or the intrinsic probability density functions and/or the fluid types determined as a result of the apparent and intrinsic probability density functions.

In some embodiments, the system 264 may include one or more displays 296 to display visual representations of the apparent and/or the intrinsic probability density functions, the apparent and/or intrinsic distributions of transverse relaxation time constants, and the diffusion distribution. The display 296 may be included as part of a surface computer 254 used to receive data from the acquisition logic 110, if desired.

The apparatus 100, 200; data 112; material 114; NMR sensors 120; signals 122; memory 124; telemetry transmitter 128; computers 136, 254; displays 132, 296; drilling rig 202; surface 204; well 206; drill string 208; rotary table 210; borehole 212; formations 214; Kelly 216; drill pipe 218; bottom hole assembly 220; drill collars 222; downhole tool 224; drill bit 226; mud pump 232; mud pit 234; hose 236; annular area 240; systems 264; tool body 270; wireline 274; drilling platform 286; derrick 288; hoist 290; logging facility 292; probe 294; and steering mechanism 298 may all be characterized as "modules" herein. Such modules may include hardware circuitry, and/or a processor and/or memory circuits, software program modules and objects, and/or firmware, and combinations thereof, as desired by the architect of the apparatus 100, 200 and systems 264, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for drilling and logging operations, and thus, various embodiments are not to be so limited. The illustrations of apparatus 100, 200 and systems 264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules, including multilayer, multi-chip modules. Such apparatus and systems may further be included as sub-components within a variety of electronic systems, such as process measurement instruments, personal computers, workstations, medical devices, vehicles, among others. Some embodiments include a number of methods.

Figure 3:
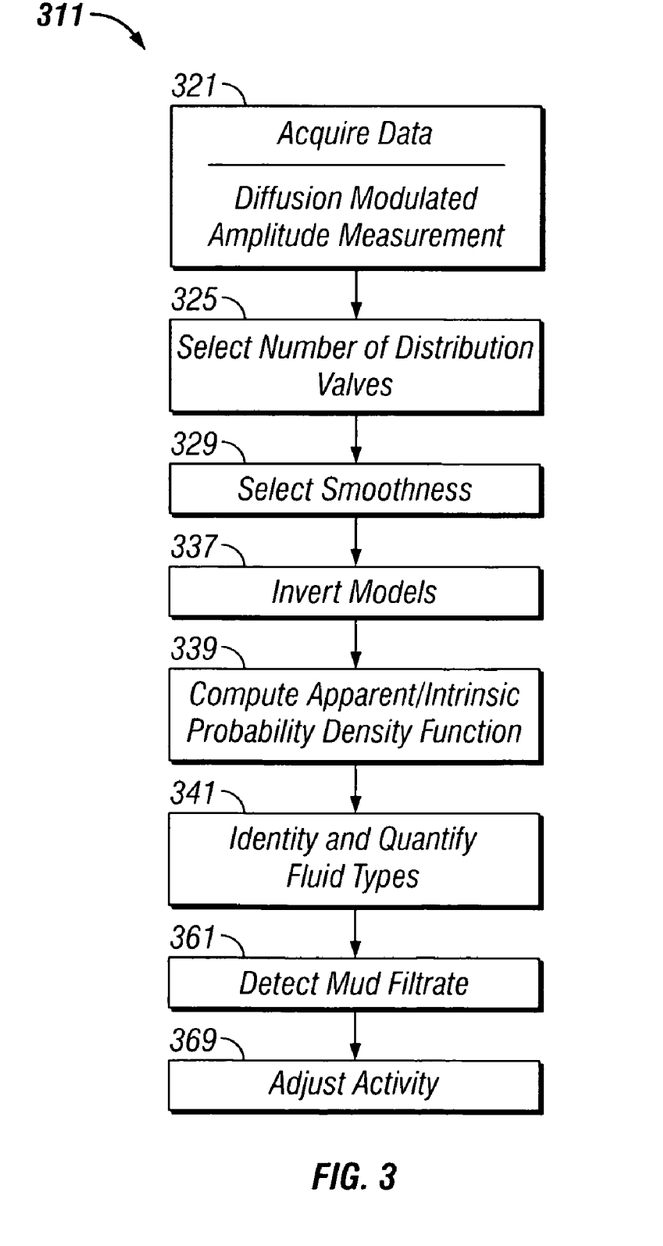
FIG. 3 illustrates a method flow diagram according to various embodiments of the invention.

For example, FIG. 3 illustrates a method flow diagram 311 according to various embodiments of the invention. In some embodiments of the invention, a method 311, such as a method of identifying fluid types in a material, may begin at block 321 with acquiring data representing a plurality of NMR echo trains associated with a material, such as a geological formation, including rock. One or more of the plurality of NMR echo trains may be characterized by a long echo spacing time $t_D$, that is approximately equal to its short echo spacing time $t_E$.

The material may include one or more fluids, such as fluids in a geological formation, or fluids that have been withdrawn from a geological formation. The data may be acquired as a portion of a DMA measurement process.

The method 311 may include selecting a number of discrete values associated with the distribution of transverse relaxation time constants and the diffusion distribution to construct the probability density function at block 325. In some embodiments, the method 311 may include selecting, independently, the smoothness of the apparent and intrinsic distributions of transverse relaxation time constants, the smoothness of the diffusion distribution, and the smoothness of the apparent and intrinsic probability density functions at block 329.

The method 311 may include, at block 337, inverting a model of at least one of the plurality of NMR echo trains to provide an estimated distribution of transverse relaxation time constants; this first inversion may result in reducing the size of the $K_2$ matrix. The method 311 may also include, at block 337, inverting models of selected ones of the plurality of NMR echo trains, using the estimated distribution of transverse relaxation time constants to provide an estimated diffusion distribution; this second inversion may result in reducing the size of the $K_1$ matrix. The method 311 may continue with inverting a model of selected ones of the plurality of NMR echo trains, using the estimated distributions of transverse relaxation time constants and diffusion, to provide an apparent probability density function to identify fluid types in the material at block 339. The method 311 may further include using the apparent probability density function to compute a plurality of intrinsic echo trains and inverting a model of selected ones of the intrinsic echo trains to provide an intrinsic probability density function at block 339.

In some embodiments, the method 311 may include identifying and quantifying the fluid types at block 341 using the probability density functions. Identifying and quantifying fluid types on a $T_2$-D map, including the apparent $T_{2A}$-D and intrinsic $T_{2I}$-D maps, is well known to those of skill in the art.

In some embodiments, the method 311 may include detecting mud filtrate contamination of fluids being withdrawn from a formation at block 361 based on the apparent and/or the intrinsic probability density functions. Detecting mud filtrate contamination of fluid types identified on a $T_2$-D map, including the apparent $T_{2A}$-D and intrinsic $T_{2I}$-D maps, is well known to those of skill in the art.

In some embodiments, the method 311 may include acquiring the data (e.g., as described with respect to block 321), and then adjusting the conduct of a drilling operation activity at block 369, such as steering the drill bit, based on the apparent and/or the intrinsic probability density functions (or fluid types identified using the apparent and/or the intrinsic probability density functions, or a model of the apparent and/or the intrinsic probability density functions). The adjustment may be made in substantially real time.

It should be noted that the methods described herein do not have to be executed in the order described, or in any particular order. Moreover, various activities described with respect to the methods identified herein can be executed in iterative, serial, or parallel fashion. Information, including parameters, commands, operands, and other data, can be sent and received, and perhaps stored using a variety of media, tangible and intangible, including one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand that various programming languages may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 4:
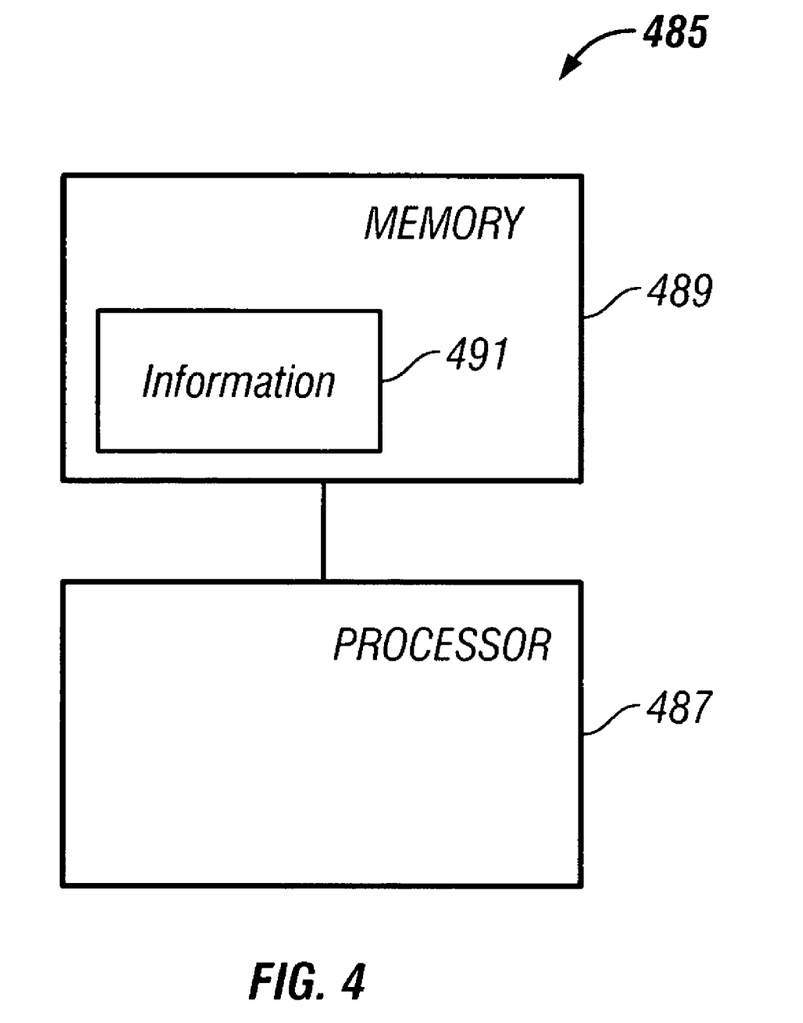
FIG. 4 is a block diagram of an article according to various embodiments of the invention.

FIG. 4 is a block diagram of an article of manufacture, or article 485 according to various embodiments, such as a computer, a memory system, a magnetic or optical disk, some other storage device, and/or any type of electronic device or system. The article 485 may include a processor 487 coupled to a computer-readable medium such as a memory 489 (e.g., fixed and removable storage media, including tangible memory having electrical, optical, or electromagnetic conductors; or even intangible memory, such as a carrier wave) having associated information 491 (e.g., computer program instructions and/or data), which when executed by a computer, causes the computer (e.g., the processor 487) to perform a method including such actions as acquiring data representing a plurality of NMR echo trains associated with a material, inverting a model of at least one of the plurality of NMR echo trains to provide an estimated distribution of transverse relaxation time constants, inverting models of selected ones of the plurality of NMR echo trains using the estimated distribution of transverse relaxation time constants to provide an estimated diffusion distribution, and inverting models of a plurality of NMR echo trains, using the estimated distributions of transverse relaxation time constants and diffusion, to provide an apparent and an intrinsic probability density function to identify fluid types in the material.

Other activities may include acquiring the data, and adjusting conduct of a drilling operation activity based on the apparent and/or the intrinsic probability density functions in substantially real time. Further activities may include determining mud filtrate contamination of fluids being withdrawn from a formation based on the apparent and/or the intrinsic probability density functions, determining whether to capture a fluid sample based on the apparent and/or the intrinsic probability density functions, and acquiring the data as a portion of a diffusion modulated amplitude measurement process, among others. In fact, any of the activities described with respect to the various methods above may be implemented in this manner.

To further demonstrate the benefits of the disclosed apparatus, systems, and methods, an example implementation will now be discussed. FIGS. 5A-5D illustrate an example probability density function 500 and accuracy of estimated data fit 510, respectively, according to various embodiments of the invention.

A data set including a plurality of NMR echo trains acquired using a magnetic resonance imaging log (MRIL) tool, similar to or identical to the formation evaluation and NMR logging tool model MRIL-Prime developed by NUMAR Corporation of Exton, Pa. The tool was immersed in a tank mixture of oil and water doped with copper sulfate, such that the transverse relaxation time distribution of the water would partly overlap that of the oil, and the following parameters were used: p=5, $t_E$=1.2, $t_D$=[2 4 10 20 40]*$t_E$, and m=382. The resulting data statistics, in terms of signal-to-noise ratio (SNR), for each of the echo trains were: [82 88 90 81 84]. There are five SNR values since five echo trains were acquired—each with a different value of $t_D$.

The tool was used to collect data from a single frequency band having a gradient G=15.0991 G/cm. The remaining tool constants were determined to be: $a_d$=0.56, and $a_s$=0.30. The following parameters were used in the inversion for both the apparent and intrinsic probability density functions: $n_1$=40, $n_2$=40, and $\tilde{\alpha}_x$=0.001, $\alpha_{x_T}$=0.01, $\alpha_{x_D}$=0.

Figure 5A:
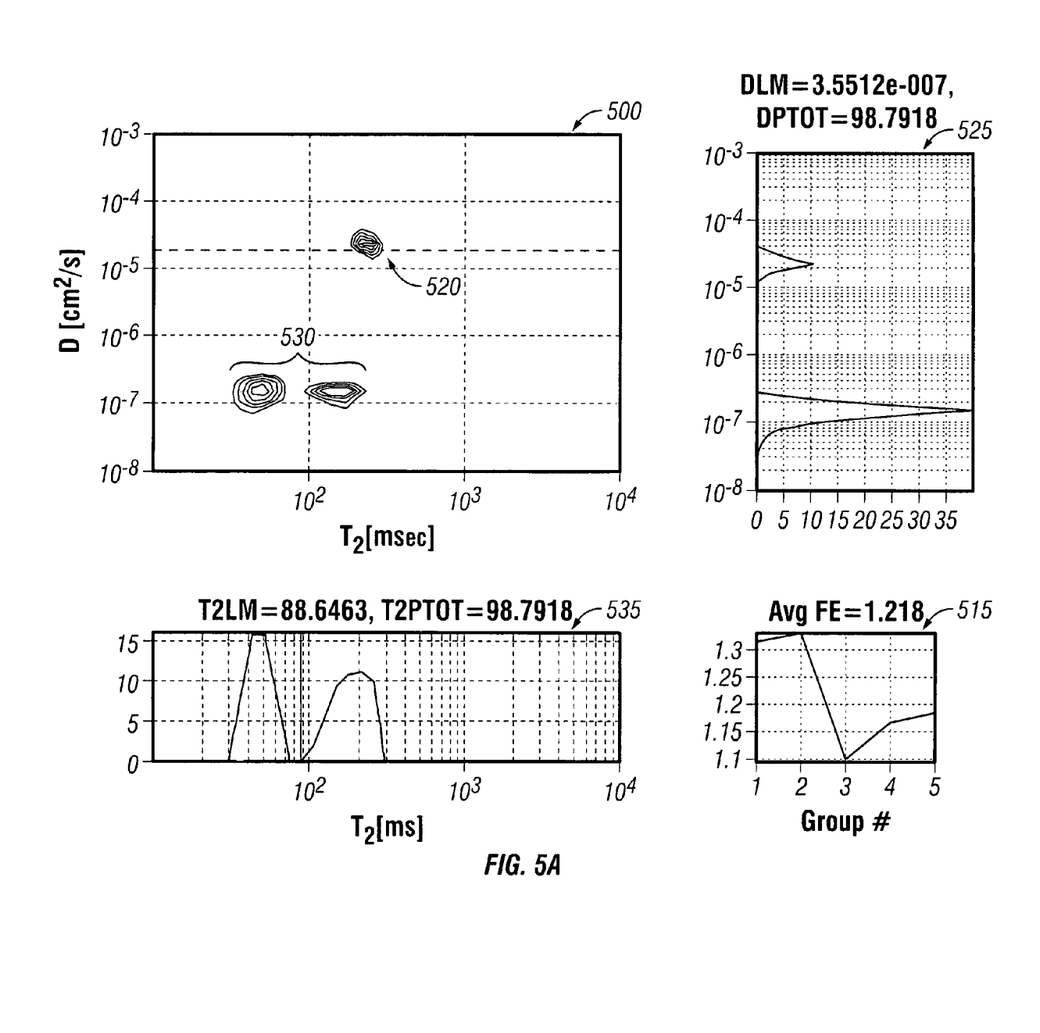
FIGS. 5A-5D illustrate an example probability density function and accuracy of estimated data fit, respectively, according to various embodiments of the invention.
Figure 5B:
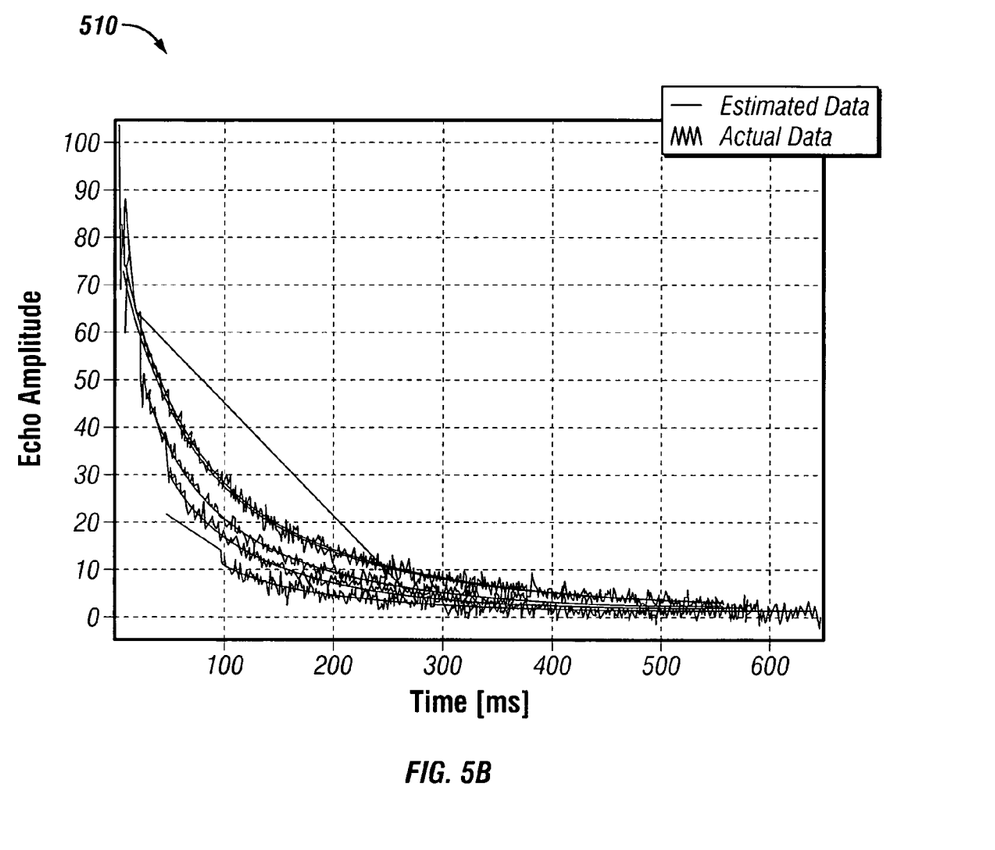

The result of plotting the function 500 as a $T_{2A}$-D map after solving for $\tilde{x}^*$ can be seen in FIG. 5A. The total computation time was about 2.5 seconds using a conventional desktop computer. As expected, the $T_{2A}$-D map indicates the presence of a mixture of two fluids: (1) a fluid 520 with a single-peak $T_2$ distribution 525 having a diffusivity value approximately equal to that expected of water at the given temperature and pressure; (2) a fluid 530 with a bi-modal $T_2$ distribution 535 having a diffusivity value slightly larger than $10^{-7}$ cm²/sec. Comparing the fit of the result to the data in FIG. 5B, the average value of the mis-fit (which is denoted as fit-error or FE 515 in FIG. 5A) for each of the five echo trains was found to be slightly greater than about 1.2.

Figure 5C:
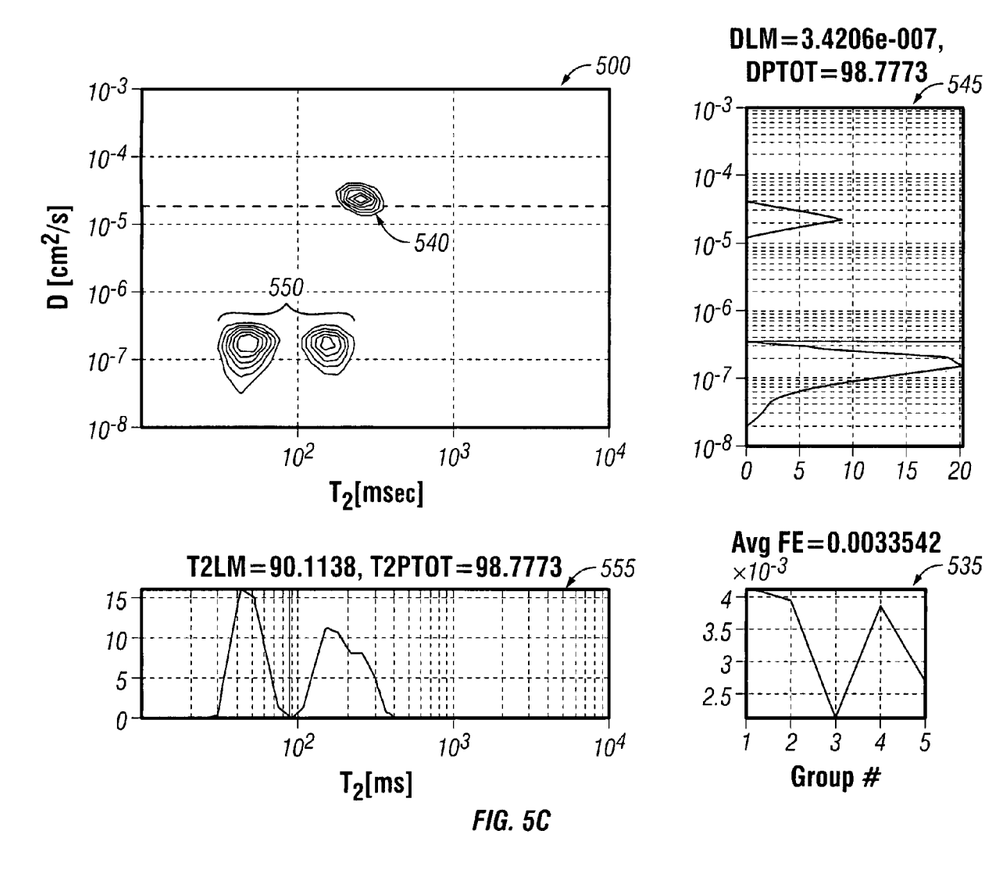
Figure 5D:
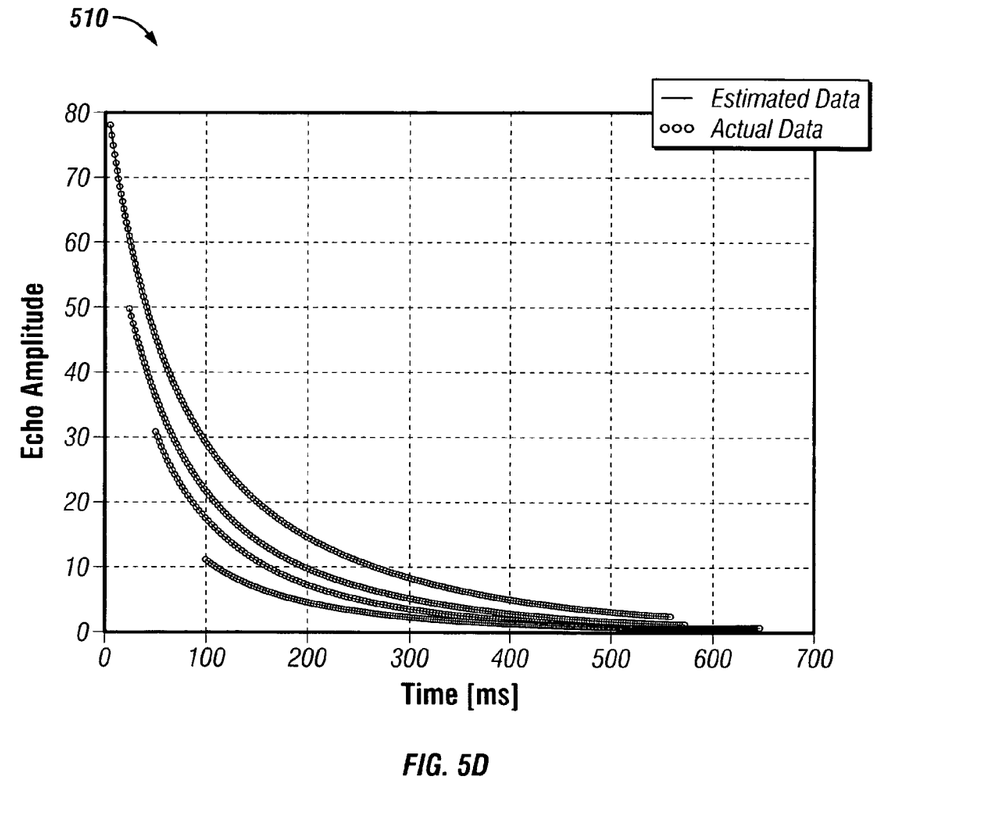

The result of plotting the probability distribution 500 as a $T_{2I}$-D map after solving for $\tilde{x}_1^*$ can be seen in FIG. 5C. The total computation time was about 10 seconds using a conventional desktop computer. As expected, the $T_{2I}$-D map indicates the presence of a mixture of two fluids: (1) a fluid 540 with a single-peak $T_2$ distribution 545 having a diffusivity value approximately equal to that expected of water at the given temperature and pressure; (2) a fluid 550 with a bi-modal $T_2$ distribution 555 having a diffusivity value slightly larger than $10^{-7}$ cm²/sec. Comparing the fit of the result in FIG. 5B to that shown in FIG. 5D, the average value of the mis-fit (denoted as FE 535 in FIG. 5C) for each of the five echo trains was found to be slightly greater than about $3*10^{-3}$.

Implementing the apparatus, systems, and methods of various embodiments may improve the process of accurately estimating the probability density functions for various fluid types. Thus, $T_2$-D maps can be provided accurately, robustly and efficiently. The proposed methodology may also provide a more optimal solution in many cases. In addition, there is greater flexibility, because the $T_2$ and diffusion distributions, as well as the probability density function, can be regularized explicitly and independently of each other and a constant regularization matrix of any form (e.g., zero, first, or second order) can be used while still preserving the linearity of the problem, affording a greater level of quantitative fluid typing confidence.

The proposed mechanism also avoids using data compression and the additional complication of the solution being dependent on the selected condition number threshold. The size of the problem is reduced in the space of the original independent variables through a sequential solution approach, which is linear throughout, reducing computational intensity. The effect of this reduction is that the unknown probability density function is preconditioned and data noise is pushed out of the solution space of the final linear problem.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A nuclear magnetic resonance apparatus, including:
  acquisition logic to acquire data representing a plurality of nuclear magnetic resonance (NMR) echo trains associated with a material; and
  processing logic to invert a model of at least one of the plurality of NMR echo trains to provide an estimated distribution of transverse relaxation time constants, to invert models of selected ones of the plurality of NMR echo trains using the estimated distribution of transverse relaxation time constants to provide an estimated diffusion distribution, and to invert models of selected ones of the plurality of NMR echo trains, using quadratic form regularization and the estimated distributions of transverse relaxation time constants and diffusion, to provide at least one of an apparent or an intrinsic probability density function to identify fluid types in the material.

2. The apparatus of claim 1, further including:
  NMR sensors to receive signals associated with the data.

3. The apparatus of claim 1, further including:
  a memory to store the data.

4. The apparatus of claim 1, wherein the data includes information associated with long echo spacing and short echo spacing for the plurality of NMR echo trains.

5. The apparatus of claim 1, further including:
  a telemetry transmitter to transmit the data to an above-ground computer.

6. The apparatus of claim 1, further including:
  a display to display visual representations of the probability density function, the distribution of transverse relaxation time constants, and the diffusion distribution.

7. A nuclear magnetic resonance system, including:
  a downhole tool;
  acquisition logic included in the downhole tool to acquire data representing a plurality of nuclear magnetic resonance (NMR) echo trains associated with a material; and
  processing logic to invert a model of at least one of the plurality of NMR echo trains to provide an estimated distribution of transverse relaxation time constants, to invert models of selected ones of the plurality of NMR echo trains using the estimated distribution of transverse relaxation time constants to provide an estimated diffusion distribution, and to invert a model of selected ones of the plurality of NMR echo trains, using quadratic form regularization and the estimated distributions of transverse relaxation time constants and diffusion, to provide at least one of an apparent or an intrinsic probability density function to identify fluid types in the material.

8. The system of claim 7; wherein the processing logic is included in the downhole tool.

9. The system of claim 7, further including:
  a wireline coupled to the downhole tool.

10. The system of claim 7, further including:
  a drill bit mechanically coupled to a drill string and the downhole tool; and
  a steering mechanism to steer the drill bit responsive to the probability density function.

11. The system of claim 10, wherein the drill string includes at least one of segmented drilling pipe, casing, and coiled tubing.

12. A method of using a nuclear magnetic resonance apparatus, including;
  acquiring data representing a plurality of nuclear magnetic resonance (NMR) echo trains associated with a material;
  inverting a model of at least one of the plurality of NMR echo trains to provide an estimated distribution of transverse relaxation time constants;
  inverting models of selected ones of the plurality of NMR echo trains using the estimated distribution of transverse relaxation time constants to provide an estimated diffusion distribution; and
  inverting a model of selected ones of the plurality of NMR echo trains, using quadratic form regularization and the estimated distributions of transverse relaxation time constants and diffusion, to provide at least one of an apparent or an intrinsic probability density function to identify fluid types in the material.

13. The method of claim 12, further including:
selecting, independently, at least two of a distribution of transverse relaxation time constants smoothness, a diffusion distribution smoothness, and a probability density function smoothness.

14. The method of claim 13, further including:
adjusting the distribution of transverse relaxation time constants smoothness, the diffusion distribution smoothness; and the probability density function smoothness to resolve the fluid types.

15. The method of claim 12, further including:
selecting a number of discrete values associated with the distribution of transverse relaxation time constants and the diffusion distribution to construct the probability density function.

16. The method of claim 12, wherein the at least one of the plurality of NMR echo trains is characterized by a long echo spacing time that is approximately equal to a short echo spacing time.

17. The method of claim 12, wherein the material comprises at least one fluid.

18. The method of claim 12, wherein the material comprises fluids within a geological formation.

19. The method of claim 12, wherein the material comprises fluids that have been withdrawn from a geological formation.

20. The method of claim 12, further including:
identifying the fluid types using the at least one apparent and intrinsic probability density function.

21. The method of claim 12, further including:
quantifying relative volumes associated with the fluid types using the at least one apparent and intrinsic probability density function.

22. A non-transitory computer readable medium having instructions stored thereon which, when executed by a computer, cause the computer to perform a method of using a nuclear magnetic resonance apparatus, comprising:
acquiring data for a plurality of nuclear magnetic resonance (NMR) echo trains associated with a material;
inverting a model of at least one of the plurality of NMR echo trains to provide an estimated distribution of transverse relaxation time constants;
inverting models of selected ones of the plurality of NMR echo trains using the estimated distribution of transverse relaxation time constants to provide an estimated diffusion distribution; and
inverting a model of selected ones of the plurality of NMR echo trains, using quadratic form regularization and the estimated distributions of transverse relaxation time constants and diffusion, to provide at least one of an apparent or an intrinsic probability density function to identify fluid types in the material.

23. The non-transitory computer-readable medium of claim 22, wherein the instructions, when executed by the computer, cause the computer to perform a method comprising:
acquiring the data; and
adjusting conduct of a drilling operation activity based on the probability density function in substantially real time.

24. The non-transitory computer-readable medium of claim 22, wherein the instructions, when executed by the computer, cause the computer to perform a method comprising:
determining mud filtrate contamination of fluids being withdrawn from a formation based on the at least one apparent and intrinsic probability density function.

25. The non-transitory computer-readable medium of claim 22, wherein the instructions, when executed by the computer, cause the computer to perform a method comprising:
acquiring the data as a portion of a diffusion modulated amplitude measurement process.

* * * * *

UNITED STATES PATENT AND TRADEMARK OFFICE
CERTIFICATE OF CORRECTION

| | | |
|---|---|---|
| PATENT NO. | : 8,044,662 B2 | Page 1 of 1 |
| APPLICATION NO. | : 12/541323 | |
| DATED | : October 25, 2011 | |
| INVENTOR(S) | : Carl-Magnus Fransson, (DECEASED) et al. | |

It is certified that error appears in the above-identified patent and that said Letters Patent is hereby corrected as shown below:

On the face page, in field (75), in "Inventors", in column 1, line 1, after "Fransson," insert -- Deceased, --.

In column 14, line 38, in Claim 8, delete "claim 7;" and insert -- claim 7, --, therefor.

In column 15, lines 8-9, in Claim 14, delete "smoothness; and" and insert -- smoothness, and --, therefor.

Signed and Sealed this
Thirty-first Day of January, 2012

David J. Kappos
*Director of the United States Patent and Trademark Office*